US009145483B2

(12) United States Patent
Hamann et al.

(10) Patent No.: US 9,145,483 B2
(45) Date of Patent: *Sep. 29, 2015

(54) POLYLACTIDE HYDROSOL AND ARTICLES MADE THEREFROM

(71) Applicants: Curtis P. Hamann, Paradise Valley, AZ (US); Sebastian S. Plamthottam, Upland, CA (US)

(72) Inventors: Curtis P. Hamann, Paradise Valley, AZ (US); Sebastian S. Plamthottam, Upland, CA (US)

(73) Assignee: SmartHealth, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/037,610
(22) Filed: Sep. 26, 2013
(65) Prior Publication Data

US 2014/0031436 A1    Jan. 30, 2014

Related U.S. Application Data

(62) Division of application No. 12/708,606, filed on Feb. 19, 2010, now Pat. No. 8,563,103.

(51) Int. Cl.

| | |
|---|---|
| *A41D 19/00* | (2006.01) |
| *A41D 19/015* | (2006.01) |
| *C08K 3/20* | (2006.01) |
| *A61B 19/04* | (2006.01) |
| *B29C 41/00* | (2006.01) |
| *B29C 41/14* | (2006.01) |
| *C08J 3/05* | (2006.01) |
| *C08J 5/02* | (2006.01) |
| *C08K 5/06* | (2006.01) |
| *C08L 67/04* | (2006.01) |
| *B29C 35/16* | (2006.01) |
| *B29L 31/48* | (2006.01) |
| *C08K 5/00* | (2006.01) |
| *C08L 5/00* | (2006.01) |
| *C08L 29/04* | (2006.01) |
| *C08L 31/02* | (2006.01) |
| *C08L 69/00* | (2006.01) |
| *C08L 71/02* | (2006.01) |
| *C08L 77/12* | (2006.01) |

(52) U.S. Cl.
CPC . *C08K 3/20* (2013.01); *A61B 19/04* (2013.01); *B29C 35/16* (2013.01); *B29C 41/003* (2013.01); *B29C 41/14* (2013.01); *C08J 3/05* (2013.01); *C08J 5/02* (2013.01); *C08K 5/06* (2013.01); *C08L 67/04* (2013.01); *B29L 2031/4864* (2013.01); *C08J 2367/04* (2013.01); *C08K 5/0016* (2013.01); *C08L 5/00* (2013.01); *C08L 29/04* (2013.01); *C08L 31/02* (2013.01); *C08L 69/00* (2013.01); *C08L 71/02* (2013.01); *C08L 77/12* (2013.01); *Y10T 428/1334* (2015.01); *Y10T 428/1345* (2015.01); *Y10T 428/1352* (2015.01); *Y10T 428/1386* (2015.01); *Y10T 428/31786* (2015.04)

(58) Field of Classification Search
None
See application file for complete search history.

(56) References Cited

U.S. PATENT DOCUMENTS

| | | | |
|---|---|---|---|
| 5,365,608 | A | 11/1994 | Flick |
| 5,438,708 | A | 8/1995 | Jacovitz |
| 5,658,969 | A | 8/1997 | Gerace |
| 5,789,031 | A | 8/1998 | Hirabayashi et al. |
| 5,849,401 | A | 12/1998 | El-Afandi et al. |
| 6,080,478 | A | 6/2000 | Karhuketo |
| 6,353,086 | B1 | 3/2002 | Kolstad et al. |
| 6,393,614 | B1 | 5/2002 | Eichelbaum |
| 6,488,948 | B1 | 12/2002 | Danieli |
| 6,521,336 | B2 | 2/2003 | Narita et al. |
| 6,756,331 | B2 | 6/2004 | Kasemura et al. |
| 6,756,450 | B2 | 6/2004 | Marinow |
| 7,455,863 | B2 | 11/2008 | Hamann |
| 7,585,526 | B2 | 9/2009 | Hamann |
| 7,619,025 | B2 | 11/2009 | Mohanty et al. |
| 2002/0094444 | A1 | 7/2002 | Nakata et al. |
| 2002/0115744 | A1* | 8/2002 | Svenningsen et al. ........ 523/122 |
| 2003/0021973 | A1 | 1/2003 | Topolkaraev et al. |
| 2003/0166754 | A1 | 9/2003 | Marinow |
| 2003/0204893 | A1 | 11/2003 | Chou |
| 2003/0216496 | A1 | 11/2003 | Mohanty et al. |
| 2004/0068059 | A1 | 4/2004 | Katayama et al. |
| 2004/0091504 | A1 | 5/2004 | Hamann |
| 2004/0091557 | A1 | 5/2004 | Hamann |
| 2005/0037054 | A1 | 2/2005 | Hamann |
| 2005/0124782 | A1 | 6/2005 | Takamura et al. |
| 2005/0221032 | A1 | 10/2005 | Yamane et al. |
| 2007/0207282 | A1 | 9/2007 | Hamann |
| 2010/0021751 | A1 | 1/2010 | Harrison et al. |
| 2010/0257657 | A1 | 10/2010 | Hamann et al. |
| 2011/0203032 | A1 | 8/2011 | Hamann et al. |

FOREIGN PATENT DOCUMENTS

| | | |
|---|---|---|
| CN | 1268865 A | 10/2000 |
| CN | 1439661 A | 9/2003 |

(Continued)

OTHER PUBLICATIONS

U.S. Appl. No. 11/138,193, filed May 26, 2005, Hamann.
Database WPI; Week 200502; Thomson Scientific, London, GB; AN 2005-016930; XP-002724283; 2005; 2 pages.
Database WPI; Week 200628; Thomson Scientific, London, GB; AN 2006-268077; XP002724284; 2006; 3 pages.
Database WPI; Week 200443; Thomson Scientific, London, GB; AN 2004-453385; XP002724285; 2004; 4 pages.
Database WPI; Week 200613; Thomson Scientific, London, GB; AN 2006-121832; XP002724286; 2006; 3 pages.
J. Van Haveren et al.; How Biobased Products Contribute to the Establishment of Sustainable, Phthalate Free, Plasticizers and Coatings; American Chemical Society ACS Symposium Series; Jan. 2006; pp. 99-115.

(Continued)

*Primary Examiner* — Ana Woodward
(74) *Attorney, Agent, or Firm* — Reinhart Boerner Van Deuren P.C.

(57) ABSTRACT

A polylactide hydrosol polymer formulations suitable for thin film articles and methods of making the thin film articles are provided. The formulations and methods can be use to make articles such as gloves, condoms, catheters and the like using dip forming, and various casting processes.

7 Claims, 2 Drawing Sheets

(56) References Cited

FOREIGN PATENT DOCUMENTS

| | | |
|---|---|---|
| DE | 4244364 A1 | 6/1994 |
| JP | H03-055812 U | 5/1991 |
| JP | H07305227 A | 11/1995 |
| JP | 2002201514 A | 7/2002 |
| JP | 2004-107413 A | 4/2004 |
| JP | 2004-339419 A | 12/2004 |
| JP | 2005008733 A | 1/2005 |
| JP | 2005082900 A | 3/2005 |
| JP | 2006-027113 A | 2/2006 |
| JP | 2006089687 A | 4/2006 |

OTHER PUBLICATIONS

State Intellectual Property Office of the People'S Republic of China; Notification of the Third Office Action; foreign Office Action dated Jun. 8, 2015; 49 pages including foreign Office Action and English language translation.

\* cited by examiner

POLYLACTIDE HYDROSOL AND ARTICLES MADE THEREFROM

CROSS-REFERENCE TO RELATED PATENT APPLICATIONS

This patent application is a divisional of U.S. Non-Provisional patent application Ser. No. 12/708,606, filed Feb. 19, 2010, the entire teachings and disclosure of which are incorporated herein by reference thereto.

FIELD OF THE INVENTION

This invention generally relates to polylactide hydrosols suitable for making thin film articles such as gloves, condoms, catheters and the like using dip forming, and various casting processes.

BACKGROUND OF THE INVENTION

Biodegradable polymers have been commercially available for a number of years. Among these polymers, polylactide (PLA) also known as polylactic acid has been used as an environmentally friendly biodegradable alternative to petroleum based polymers such as polyvinyl chloride (PVC), polyethylene terephthalate (PET), high impact polystyrene (HIPS), polyethylene (PE), and polypropylene (PP), in applications such as rigid and flexible packaging, candy wraps, shrink labels, and form-fill seal extrusions. Further, polylactide has been extensively studied in medical implants, suture, and drug delivery systems due to its biodegradability and has been approved for use in various medical devices. Different thermoplastic processes such as extrusion, blow molding, injection molding, and spinning processes are used to make these products. However, the manufacturing cost of thin articles having complex shapes and sizes, such as gloves, condoms, catheters, using PLA has been prohibitably high, or the PLA thin articles were not substantially biodegradable due to non-biodegradable ingredients in PLA formulations.

Polylactic acid polymers can be manufactured from renewable resources, unlike conventional, synthetic petroleum-based polymers, since the lactate from which it is ultimately produced can be derived from fermentation of agricultural by-products such as corn starch or other starch-rich, substances like sugar or wheat. Lactate which is also known as Lactic acid is a natural molecule that is widely employed in foods as a preservative and a flavoring agent. It is the main building block in the chemical synthesis of the polylactide family of polymers. Although it can be synthesized chemically, Lactic acid is procured principally by microbial fermentation of sugars such as glucose or hexose. These sugar feed stocks can be derived from potato skins, corn, wheat, and dairy wastes.

Lactic acid exists essentially in two stereoisomeric forms, which give rise to several morphologically distinct polymers: D-polylactic acid, L-polylactic acid, D,L-polyactic acid, meso-polylactic acids, and any combinations thereof. D-polylactic acid and L-polylactic acid are stereoregular polymers. D,L-polylactic acid is a racemic polymer obtained from a mixture of D- and L-lactic acid, and meso-polylactic acid can be obtained from D,L-lactide. The polymers obtained from the optically active D and L monomers are semicrystalline materials, but the optically inactive D,L-polylactic acid is substantially amorphous.

Degradation of PLA occurs in two stages. First, the ester groups are gradually hydrolyzed by water to form lactic acid and other small molecules, and then these products are decomposed by microorganisms in the environment. In addition, disposal of PLA products is easier than that of traditional polymers, because polylactic acid incinerates cleanly with lower energy yield, thereby permitting a higher incinerator facility throughput. Further, PLA contains no chlorine or aromatic groups, so PLA burns much like paper, cellulose, and/or carbohydrates—generating few combustion by-products.

Disposable gloves are widely used by members of the medical community, the scientific community, and the industrial community to protect the wearer from chemical exposure, mechanical abrasion, environmental hazards, biohazard contamination and to prevent transmission of disease or contaminants. Health care providers frequently wear disposable gloves while performing surgery or other medical or dental procedures such as patient examinations; thus, the gloves are often also referred to as disposable examination gloves or disposable surgical gloves. The disposable gloves are impermeable to biological fluids, tissues and solids produced by the body or other contaminants (human or animal) advantageously protecting the wearer from fomitic (transmission by objects that harbor pathogenic organisms) transmission of pathogens and disease.

Also, disposable gloves are worn by individuals who wish to protect their hands from various chemicals, materials and objects which may irritate, damage or dry out the users skin and which may be harmful or potentially harmful if allowed to contact or permeate the dermal barrier. These gloves may be worn in the occupational setting by scientists, cleaning service workers, food handlers, law enforcement workers, beauticians or other workers having special protection needs. Thus, disposable gloves may also be referred to as protective gloves or industrial gloves. Also some disposable gloves are considered reusable gloves because they can be used multiple times prior to disposal. For example, homemakers may reuse the same pair of household gloves to protect their hands from harsh cleaning solutions or just while washing dishes. Likewise, gardeners or plant service workers may reuse gloves when spraying plants with fungicides or other garden chemicals.

As is known in the art, disposable gloves (and reusable gloves as well as other flexible elastomer articles) are thin and flexible and are manufactured from a variety of polymeric materials herein throughout referred to as "elastomer(s)" or "elastomer material(s)" or "raw material(s)". These elastomers may be considered a natural rubber as with natural rubber latex (NRL) or a synthetic rubber, or a plastic and include, but are not limited to, a synthetic polyisoprene, a chloroprene (including Neoprene-homopolymer of the conjugated diene chloroprene), a polyurethane (PU), a polyvinyl chloride (PVC), a styrene butadiene styrene (SBS), a styrene isoprene styrene (SIS), a silicone, a butadiene methylmethacrylate, an acrylonitrile, a styrene ethylene butylene styrene (SEBS), an acrylate-based hydrogel, any other elastomer that can be suspended into an emulsion, any other elastomer that is suspendable, soluble or miscible in a solution or plastisol, and combinations thereof.

Regardless of the type of end use application and/or specific thermoplastic used, elastomeric gloves are typically thrown away after a single use, and therefore, a significant amount of waste is generated.

Importantly, many of the polymers utilized in manufacturing disposable gloves are petroleum based and resist environmental degradation. Indeed, the environmental impact of nonbiodegradable plastic waste is a growing concern and alternative disposal methods for such plastics are limited. For example, incineration of synthetic plastics generates toxic emissions and satisfactory landfill sites are becoming increasing limited.

Further, petroleum resources are finite. Indeed, as petroleum reserves decrease in abundance, the raw material and production costs associated with the manufacture of such nonbiodegradable, thermoplastic gloves will increase accordingly. In addition, government regulations may increase disposal and recycling costs for nonbiodegradable plastics to accommodate landfilling and/or environmental impact resulting from use of such materials.

Biodegradable disposable gloves are only very generally known in the art. In particular, PLA is more expensive than many petroleum-derived commodity plastics, and, as such, use of PLA for disposable medical and/or industrial gloves is cost prohibitive—especially given the sheer number of disposable gloves utilized, for instance, in hospitals and clinics. Further, carcinogenicity and toxicity concerns related to the use of certain plasticizers have previously taught against use of PLA polymers in the production of disposable medical gloves.

U.S. Pat. No. 6,393,614 to Eichelbaum discloses a disposable, loose-fitting glove with pockets for carrying an item such as a tampon or sanitary napkin from a patient. While the glove is recited to be biodegradable in theory, no material of construction or degradability specifications are disclosed or suggested. Indeed, the '614 patent does not enable or provide a description of the biodegradable materials or methods of construction/manufacturing considered within the scope of the invention.

U.S. Patent Publication No. 2007/0207282 assigned to the present assignee discloses a polylactic acid glove and method of making the same, the teachings and disclosures of which is hereby incorporated by reference in their entireties to the extent not inconsistent with the present disclosure.

The invention provides improved biodegradable thin articles such as elastomeric gloves and methods of making the same. These and other advantages of the invention, as well as additional inventive features, will be apparent from the description of the invention provided herein.

BRIEF SUMMARY OF THE INVENTION

Improved biodegradable polylactide (PLA) thin articles made from PLA hydrosols and method of making the same using dip forming and rotational casting type processes are provided. A 'green' dispersion such as a waterborne dispersion or a hydrosol can allow for elimination of the use of organic solvents and provide manufacturing processes that are environmentally friendly.

In one aspect, the invention provides a glove that includes at least one layer of an elastomeric material. The elastomeric material includes a polylactic acid polymer and a non-ionic surfactant. In one embodiment, the glove is a biodegradable glove comprising a plurality of layers of an elastomeric material, wherein each of the layers of the elastomeric material includes the polylactic acid polymer and the non-ionic surfactant. In other embodiments, the glove is a disposable medical glove.

The polylactic acid polymer in the elastomeric material is selected from the group consisting of D polylactic acid, L polylactic acid, D,L polylactic acid, meso polylactic acid, and any combinations thereof. The elastomeric material can further include a biodegradable polymer resin selected from the group consisting of homopolymers, block copolymer, graft copolymer, random copolymer polyblend and combinations thereof, wherein the polyblend is selected from the group consisting of polyglycolic acid, polycaprolactone, polyhydroxybutyrate, aliphatic polyesters, polyalkylene esters, polyester amides, polyvinyl esters, polyester carbonates, polyvinyl alcohols, polyanhydrides, polysaccharides, and combinations thereof.

In one embodiment, the non-ionic surfactant is an Octyl phenol ethoxylate. In such embodiments, the elastomeric material can include the polylactic acid polymer between about 50%-99% by weight and the Octyl phenol ethoxylate between about 1%-50% by weight.

In other embodiments, the non-ionic surfactant comprises a polyethylene glycol. The non-ionic surfactant can further include an Octyl phenol ethoxylate in addition to the polyethylene glycol.

In some embodiments, the elastomeric material can further include a plasticizer. The plasticizer can be selected from the group consisting of a polyethylene glycol, a polypropylene glycol, a fatty acid ester, a citric acid ester, a lactide monomer, an epoxidised oil, an adipate ester, an azealate ester, an acetylated coconut oil, an Octyl phenol ethoxylate, and any combinations thereof.

In embodiments, wherein the elastomeric material includes the polylactic acid polymer and an Octyl phenol ethoxylate, the Octyl phenol ethoxylate provides a dual function of the non-ionic surfactant and the plasticizer. Wherein the elastomeric material further includes a polyethylene glycol, each of the Octyl phenol ethoxylate and the polyethylene glycol provides the dual function of the non-ionic surfactant and the plasticizer.

In some embodiments, the elastomeric material is formed from a hydrosol including the polylactic acid polymer and the non-ionic surfactant; wherein the hydrosol further includes at least one of a defoaming agent, a cross-linking agent, a chain extender, an aging and hydrolytic stabilizer for PLA, a flavoring component, an antimicrobial agent, a detackifying agent, a botanical extract, a donning enhancing agent, a colorant component, and a therapeutic component.

In another aspect, the invention provides a method of making a thin article. The method includes steps of preparing a hydrosol including a polylactide polymer and forming a thin article using the hydrosol.

In one embodiment, the step of preparing a hydrosol involves preparing a polylactic acid polymer powder, preparing a non-ionic surfactant, and dispersing the polylactic acid polymer powder and the non-ionic surfactant in water to form a hydrosol. The preparation of a polylactic acid polymer powder can involve grinding polylactic acid polymer pellets into powder having an average particle size less than 1000 microns. Grinding of polylactic acid polymer pellets can be performed via cryogenic milling, ambient milling, jet milling, or micro grinding. The dispersion can be prepared by mixing the polylactic acid polymer powder, the non-ionic surfactant and water using a high shear blender, rotor/stator assembly or a homogenizer.

In another embodiment, a plasticizer is dispersed in water with the polylactic acid polymer powder and the non-ionic surfactant to form a hydrosol.

In one embodiment, the step of preparing a hydrosol comprises dispersing a polylactic acid polymer powder and an Octyl phenol ethoxylate in water to form a hydrosol, wherein the hydrosol includes between about 30-40% by weight of the polylactic acid polymer powder, between about 0.3-3% by weight of the Octyl phenol ethoxylate, and between about 60-70% by weight of water. The step of forming a thin article can involve casting a film using the hydrosol, drying at a temperature between about 65° C.-90° C. to evaporate water from the hydrosol, and fusing at a temperature between about 125° C.-200° C. to form a rigid film.

In another embodiment, the step of preparing a hydrosol comprises dispersing a polylactic acid polymer powder and an Octyl phenol ethoxylate in water to form a hydrosol, wherein the hydrosol includes between about 20-40% by weight of the polylactic acid polymer powder, between about 5-20% by weight of the Octyl phenol ethoxylate, and between about 40-70% by weight of water. The step of forming a thin article can involve heating a glove former to a temperature between about 60° C.-75° C., dipping the pre-warmed glove former into the hydrosol, drying the hydrosol deposited on the glove former at a temperature between about 65° C.-90° C. to evaporate water, and fusing at a temperature between about 125° C.-200° C. to form an elastomeric glove. In some embodiments, the step of forming a thin article further includes repeating dipping the glove former in a hydrosol after drying and before fusing to form a second layer, and repeating drying to evaporate water from the second layer, wherein the elastomeric glove includes two or more elastomeric layers. In such embodiment, the glove former deposited with the hydrosol and dried can be dipped in a second hydrosol that has a different formulation than the hydrosol deposited first, wherein the elastomeric glove formed includes two or more layers, each layer having a different elastomeric formulation than the other layer.

In yet another aspect, the invention provides a polylactic acid polymer hydrosol. The hydrosol includes a polylactic acid polymer powder and a non-ionic surfactant, wherein the polylactic acid polymer powder and the non-ionic surfactant is dispersed in water.

In one embodiment, the non-ionic surfactant is an Octyl phenol ethoxylate, and the hydrosol includes the polylactic acid polymer powder between about 30-40% by weight, the Octyl phenol ethoxylate between about 0.3-3% by weight, and water between about 60-70% by weight.

In another embodiment, the non-ionic surfactant is an Octyl phenol ethoxylate, and the hydrosol includes the polylactic acid polymer powder between about 20-40% by weight, the Octyl phenol ethoxylate between about 5-20% by weight, and water between about 40-70% by weight.

In yet another embodiment, the non-ionic surfactant comprises a polyethylene glycol.

In some embodiments, the hydrosol further includes a plasticizer, wherein the plasticizer is dispersed in water with the polylactic acid polymer powder and the non-ionic surfactant. In such embodiments, the hydrosol can include an Octyl phenol ethoxylate, wherein the Octyl phenol ethoxylate is both the non-ionic surfactant and the plasticizer. The plasticizer can be selected from the group consisting of a polyethylene glycol, a polypropylene glycol, a fatty acid ester, a citric acid ester, a lactide monomer, an epoxidised oil, an adipate ester, an azealate ester, an acetylated coconut oil, an Octyl phenol ethoxylate, and any combinations thereof.

In one embodiment, the hydrosol further includes at least one of a defoaming agent, a cross-linking agent, a chain extender, an aging and hydrolytic stabilizer for PLA, a flavoring component, an antimicrobial agent, a detackifying agent, a botanical extract, a donning enhancing agent, a colorant component, and a therapeutic component.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

The following disclosure will detail particular embodiments according to the present invention, which provide biodegradable thin articles and methods of making the same. More particularly, hydrosols including polylactide (PLA), which are suitable for making thin flexible articles, such as gloves, condoms, catheters, etc., using dip forming or rotational casting type processes and methods of making the same are provided. Although, the PLA hydrosols of embodiments presented herein are particularly suitable for forming flexible articles, in other embodiments, the PLA hydrosol can also be used to form rigid film(s) or article(s).

It has been known that degradation of polylactide occurs in the presence of water at elevated temperatures. Therefore, manufacturing processes of polymeric articles using PLA hydrosols, which are essentially PLA dispersion in water, were unknown as such processes require a combination of PLA, water, and elevated temperatures. Despite, this conventional wisdom, embodiments of the present invention provides methods of making biodegradable articles using PLA hydrosols.

A flexible elastomer article (herein also "article" or "articles" or "flexible articles" or "flexible article" or flexible (articles)) of the present invention has at least one layer of an elastomer comprising polylactide (PLA). The article has a wearer contacting surface and an opposite distal surface. The distal surface is disposed as the most opposite surface to the wearer contacting surface. (The distal surface is disposed distal to the wearer contacting surface.) In some instances for certain articles, the distal surface is referred to as the outer surface or outer distal surface. However, for some articles, such as catheters, the distal surface may be the innermost surface.

The flexible article(s) of the present invention include, but are not limited to, a glove (reusable or disposable), a catheter, a stent or an incontinence device having a sheath or sheath type construction, a condom, a cervical cap, a diaphragm, a dental dam, an elastomer sheet, a sheath or tube for use with a medical device, a finger cot, or a balloon for use in a medical device (such as, but not limited to, a balloon used with a balloon catheter, a urinary catheter, a rectal catheter, an endotracheal tube, a feeding tube, or a cardiac catheter).

Figure 1:
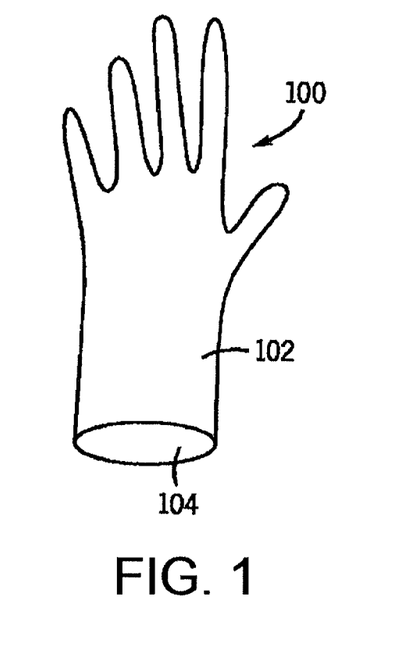
FIG. 1 is a perspective view of a glove according to an embodiment of the present invention showing an outer surface thereof and an inner or wearer-contacting surface thereof.

FIG. 1 shows an elastomeric article in the form of a glove 100 according to an embodiment of the present invention. The glove 100 includes an outside surface (distal surface or outer distal surface or outermost surface) 102 and an inside or wearer-contacting surface 104. It will be appreciated by those skilled in the art, for purposes of the following discussion, the glove 100 may be a single layer glove, a bilaminar glove (two layers), and/or a multilayer glove wherein the exterior appearance of the glove 100 is substantially similar to that shown in FIG. 1, having an outside surface 102 and wearer-contacting surface 104.

The glove 100 is a biodegradable glove, wherein an elastomeric material of the glove 100 is formed from a polylactide hydrosol. The polylactide hydrosol is a waterborne dispersion comprising polylactide polymers. In one embodiment, the polylactide hydrosol is prepared by dispersing a polylactide polymer powder, a non-ionic surfactant, and water. In some embodiments, the polylactide hydrosol also includes a plasticizer compatible with the polylactide polymer.

Figure 3:
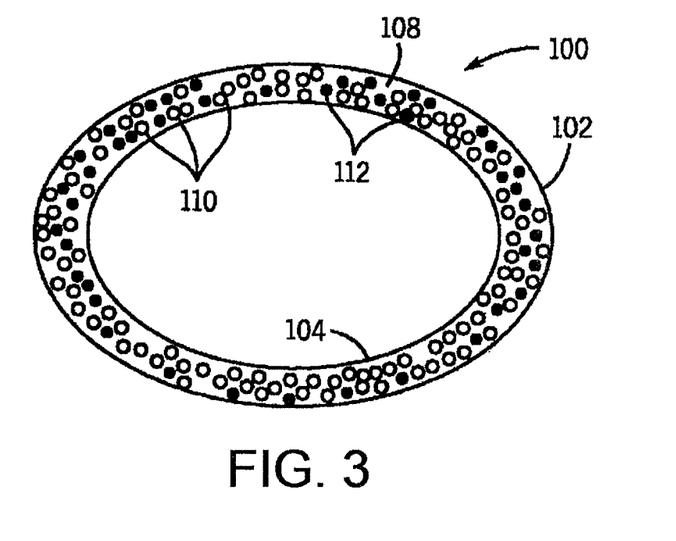
FIG. 3 is a cross sectional view of a portion of the glove of FIG. 1 having a single layer according to an embodiment of the present invention.

The polylatide polymer can comprise polymers of lactic acid or lactide, the repeating unit could be L-lactide, D-lactide, or meso lactide, or R or S lactic acid and/or copolymers of D, L, or meso lactide monomers or R or S lactic acid monomers. Depending on the structure of the PLA, it can be amorphous, crystalline or a mixture of both. Monomers that make up the polylactic acid polymer can be about 1% to about 100% L-lactide monomer, with the remaining monomer selected from, but not limited to, D lactide, meso D, L lactide, D, L lactide monomers, and combinations thereof. Consistent with the broader aspects of the present invention, the polylactic acid polymer component 110 can be any homopolymer of lactic acid and/or a block, graft, random, copolymer, and/or a polyblend/elastomeric blend of lactic acid, including, D polylactic acid, L polylactic acid, D, L polylactic acid, meso polylactic acid, and any combination of D polylactic acid, L polylactic acid, D, L polylactic acid, and meso polylactic acid. Examples of such polymers include Ingeograde PLA polymer pellets from NatureWorks LLC and Ecorene PLA powders from ICO Polymers. In other embodiments, the hydrosol can include copolymers of PLA or blends with other biodegradable polymers.

The particular weight percent of L lactide, D lactide, meso D, L Lactide, and/or D, L lactide monomer utilized in a polymer dispersed in a polylactide hydrosol of the present invention can depend on a given end use application of a flexible article to be formed, e.g. the physical and/or permeability requirements of the flexible article, the amount and/or type of plasticizer utilized and/or a specified degradation rate required for the flexible article after disposal.

Indeed, as will be appreciated by those skilled in the art, a higher concentration of D lactide monomer included within the polylactic acid polymer can result in a polymer of greater crystallinity, yielding a higher tensile strength and lowering the elongation modulus of the flexible article such as a glove. As such, the concentration of a particular lactide monomer can be varied, as a matter of design choice, depending on the desired physical, chemical and/or degradation properties required for the particular application.

Figure 2:
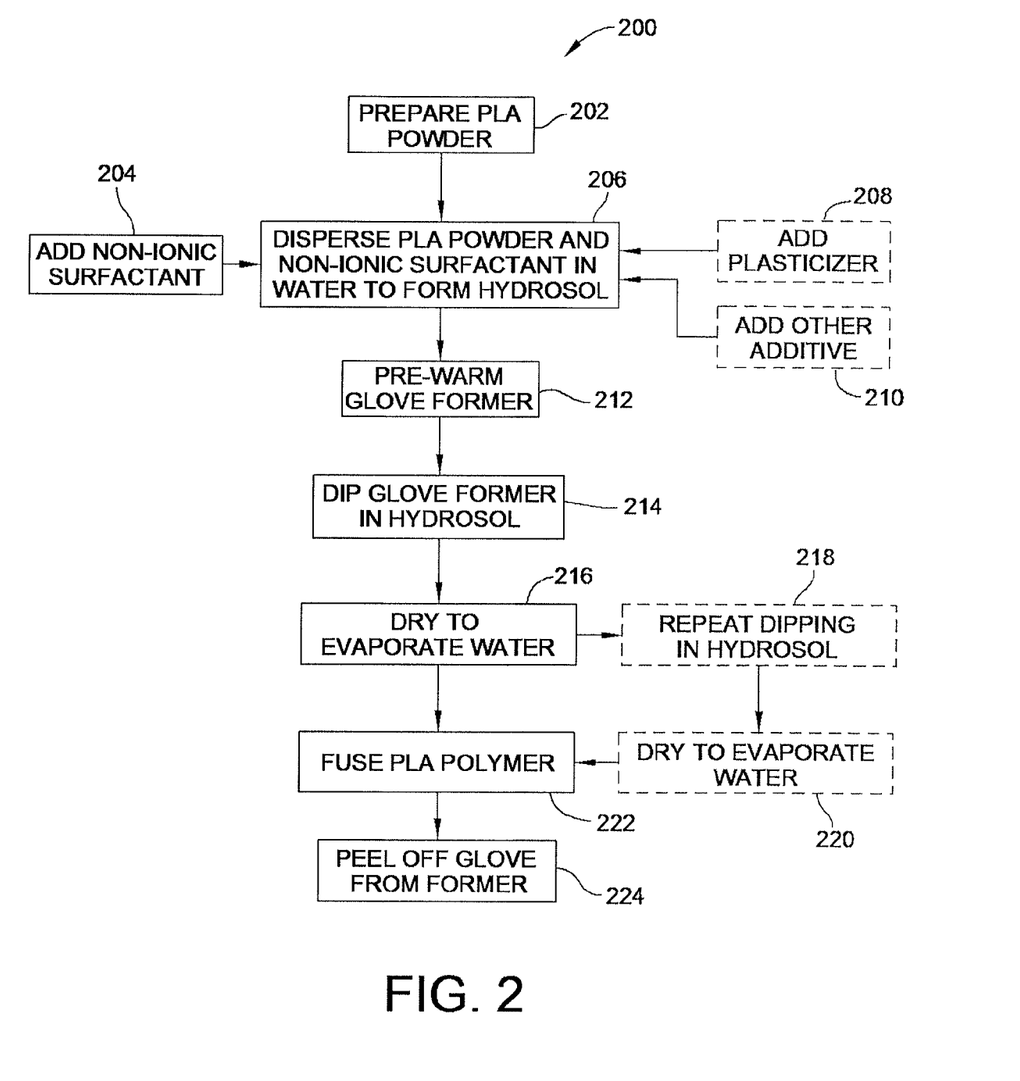
FIG. 2 is a flow diagram of a method of making the glove of FIG. 1 using a PLA hydrosol according to an embodiment of the present invention.

FIG. 2 is a flow chart illustrating a method of making a glove 200 according to an embodiment of the present invention. The method 200 generally includes steps of preparing a PLA powder 202, adding a non-ionic surfactant 204, dispersing the PLA powder and the non-ionic surfactant in water to form a hydrosol 206, pre-warming a glove former 212, dipping the pre-warmed former in the hydrosol 214, drying the hydrosol deposited on the former to evaporate water 216, fusing the PLA polymer 218, and peeling off the glove formed on the former 224. In some embodiments, the method 200 can include optional steps of adding a plasticizer 208 and other additives 210 in the PLA hydrosol. Further, the dipping and drying steps can be repeated 218, 220 to form multilayer gloves.

The polylactide (PLA) polymer powder can be prepared via various grinding or pulverizing techniques. Grinding of PLA polymer pellets can be carried out at ambient or cryogenic temperatures, preferably, at a temperature substantially below the glass transition temperature of the PLA polymer. In one embodiment, the PLA polymer is obtained in the form of pellets and processed into powder by cryogenic milling. In other embodiments, other suitable size reduction techniques such as ambient milling, jet milling, and/or micro grinding techniques can be used to prepare the PLA powder. The grinding technique can be selected according to the characteristics of the PLA polymer and a desired range of particle size. For example, a PLA polymer having a low glass transition temperature may require cryogenic milling. In one embodiment, the PLA powder has an average particle size below 1000 microns, preferably below 100 microns, more preferably below 50 microns.

The PLA powder is dispersed in water with a non-ionic surfactant to form a PLA hydrosol. The dispersions can be made using a high shear blender or a rotor/stator assembly or a homogenizer such as IKA Ultra Turrax T-25 available from IKA Works, Inc. to form a fine dispersion or hydrosol. Surprisingly, such PLA hydrosol forms strong stable thin coherent films after drying and fusing when cast or dip formed into a thin article.

In one embodiment, a stable hydrosol can be made from the PLA powder by dispersing the powder in water in the presence of a non-ionic surfactant and using a homogenizer or disperser. Preferably, the non-ionic surfactant that is compatible with the PLA polymer is selected. Further, the non-ionic surfactant is preferably substantially biodegradable. A suitable non-ionic surfactant includes Octyl phenol ethoxylates where the hydrophilic repeat unit x varies from x=4.5 to x=55. Lower the x value, less soluble it is in water. The hydrocarbon group R is commonly Octyl, but other hydrocarbon groups can be substituted as long as the substituted surfactant is compatible with the selected PLA powder and stable in the dispersion. Other suitable non-ionic surfactants include, but not limited to, certain polyethylene glycols such as Carbowax™ 3300, Carbowax™ 8000, Carbowax™ 20000 available through the Dow Chemical Company and the like. Other surfactants known in the art are equally suitable if it forms a stable dispersion and does not substantially degrade the polymer during use.

In one embodiment, a plasticizer is added in the hydrosol formulation. The plasticizer is preferably substantially biodegradable. A suitable plasticizer includes, but not limited to, polyethylene glycol, polypropylene glycol, fatty acid esters, citric acid esters such as acetyl tributyl citrate, triethyl citrate, acetyl triethyl citrate, lactide monomer, epoxidised oils such as epoxidsied soybean oil, epoxidised linseed oils, adipate esters, azealate esters, acetylated coconut oil, and the like. Octyl phenol ethoxylate, which was discussed above as a suitable non-ionic surfactant for dispersing PLA powder in water, has not been known as a plasticizer for polymeric formulations for forming elastomeric articles. Surprisingly, experiments have shown that Octyl phenol ethoxylate type compounds can also plasticize the PLA. Therefore, in some embodiments, Octyl phenol ethoxylates can provide a dual function in the PLA hydrosol as a non-ionic surfactant and a plasticizer. Such hydrosol can produce highly biodegradable thin articles. Other compounds such as polyethylene glycols can also be used as both a non-ionic surfactant and a plasticizer in forming a PLA hydrosol.

Other additives such as defoaming agents, cross-linking agents, chain extenders, aging and hydrolytic stabilizers for PLA could also be added to the PLA hydrosol, if desired, to improve processability and physical properties, and to control aging and biodegradability.

In one embodiment, a PLA hydrosol is prepared by dispersing a polylactic acid polymer powder and an Octyl phenol ethoxylate in water, wherein the hydrosol includes between about 30-40% by weight of the polylactic acid polymer powder, between about 0.3-3% by weight of the Octyl phenol ethoxylate, and between about 60-70% by weight of water. A rigid film can be formed by casting a film using the such PLA hydrosol, drying at a temperature between about 65° C.-90° C. to evaporate water from the PLA hydrosol, and fusing the film at a temperature between about 125° C.-200° C.

In another embodiment, a PLA hydrosol is prepared by dispersing a polylactic acid polymer powder and an Octyl phenol ethoxylate in water to form a hydrosol, wherein the hydrosol includes between about 20-40% by weight of the polylactic acid polymer powder, between about 5-20% by weight of the Octyl phenol ethoxylate, and between about 40-70% by weight of water. A flexible elastomeric glove can be formed using the such PLA hydrosol by heating a glove former to a temperature between about 60° C.-75° C., dipping the pre-warmed glove former into the hydrosol, drying the hydrosol deposited on the glove former at a temperature between about 65° C.-90° C. to evaporate water, and fusing the elastomeric layer formed from the PLA hydrosol at a temperature between about 125° C.-200° C.

Depending on desired characteristics of a thin article, the viscosity of the PLA hydrosol can be controlled by adjusting an amount of water, selecting a particular plasticizer type, controlling an amount of the plasticizer, and selecting a particular surfactant. For example, when making a glove by dipping a former into a PLA hydrosol, the thickness of the glove can be controlled by adjusting the viscosity, dipping and rotational speed and duration, etc. A thicker glove can be obtained by increasing the viscosity of the PLA hydrosol.

In one embodiment, the glove 100 can be formed using a glove former. For example, the step of pre-warming a glove former 212 can include heating a ceramic or aluminum glove former of a desired size to about 60° C. to 75° C. The pre-warmed glove former can then be gently immersed in the PLA hydrosol to produce a continuous uniform deposit of the dispersion on the former in the step 214. The former can be subjected to a rotational and wavy motion to distribute the dispersion evenly on the former.

In one embodiment, an elastomeric layer formed by such dipping process is about 0.03 to 2 millimeters thick. The thickness of the elastomeric layer can be controlled by adjusting various process parameters such as viscosity of the PLA hydrosol, duration of the former immersed in the PLA hydrosol, rotational speed of the former, etc. The dipped glove former is heated to a moderate temperature to evaporate water in the step 216 of FIG. 2. In one embodiment, the glove is dried at a temperature between about 65° C. and about 90° C. By evaporating water at such moderate drying temperatures, the hydrolytic degradation of the PLA polymer, which occurs at higher temperatures, can be minimized.

After water in the PLA hydrosol deposited on the former has been evaporated in the drying step 216, the PLA layer formed on the glove former is fused at a higher temperature in the step 222. In one embodiment, the PLA layer is heated to between about 125° C. and about 200° C. for several minutes. The temperature and duration of the fusing step 222 depend on a formulation of the PLA hydrosol. For example, highly plasticized compositions and those containing amorphous PLA fuses at a lower temperature than an unplasticized and crystalline PLA. The fusion temperature is normally substantially above a glass transition temperature of the PLA composition.

After the PLA polymer has been fused, the glove 100 can be peeled off from the glove former. The glove 100 formed according to this embodiment has a single layer 108 as shown in FIG. 3. In one embodiment, wherein the PLA hydrosol is formed by dispersing a PLA powder in the presence of Octyl phenol ethoxylate in water, wherein Octyl phenol ethoxylate acts as both a non-ionic surfactant and a plasticizer, the layer 108 comprises a PLA component 110 and an Octyl phenol ethoxylate 112 component.

Further, consistent with the broader aspects of the present invention, the layer 108 may include additional components incorporated into the elastomeric component of the glove 100, or coated on one or more surfaces 102, 104 of the glove 100. For example, the PLA hydrosol can be prepared to include flavoring agents, detackifying agents, donning enhancing agents, and/or botanical components. For example, xylitol as described in more detail in U.S. patent application Ser. No. 11/138,193, and Aloe extract and Nopal extract as described in more detail in U.S. Pat. Nos. 7,455,863 and 7,585,526 and U.S. Patent Publication No. 2005/0037054, which are assigned to the assignee of the present patent application and incorporated herein by reference, can be mixed in the PLA hydrosol to form the glove 100.

In addition, the PLA hydrosol for forming the glove 100 can be formulated to include one or more therapeutic components having one or more therapeutic components having one or more qualities of wound healing, anti-inflammatory properties, and antimicrobial properties. In addition, the layer 108 of the glove 100 can be colored by including a colorant in the PLA hydrosol. Such components are selected to be compatible with the PLA polymer and other components in the PLA hydrosol such as the non-ionic surfactant and the plasticizer.

In other embodiments, the glove 100 can be coated with one or more optional components after the fusing step 222. The optional coating components can include, but not limited to, flavoring, xylitol, Aloe, Nopal, vitamin E, vitamin A, vitamin C, vitamin $B_3$, vitamin $B_5$, jojoba, rose hip, tea tree oil, flax seed oil, palm oil, and/or actylsalicylic acid.

In other embodiments, the dipping process can be repeated prior to the fusing step 222 to form a multilayer glove as shown in steps 218 and 220 of the method 200. For example, the dipping and drying process can be repeated three times to form a 3-layer glove. Each of the layers can be formed of a same PLA hydrosol or different PLA hydrosols. In one embodiment, the pre-warmed former can be dipped in a first PLA hydrosol and dried, then subsequently dipped into a second PLA hydrosol that is a different formulation than the first PLA hydrosol to form a 2-layer glove having different PLA hydrosol formulation layers.

In one embodiment, a glove is formed from a PLA hydrosol. The glove includes at least one layer of an elastomeric material that includes a polylactic acid polymer between about 50%-99% by weight and the Octyl phenol ethoxylate between about 1%-50% by weight. In another embodiment, a biodegradable glove includes a plurality of layers of an elastomeric material, and each of the layers of the elastomeric material includes a polylactic acid polymer and a non-ionic surfactant. The glove can be a disposable medical glove.

EXAMPLES

The following examples illustrate applications and practices according to embodiments of the present invention. These examples are presented by way of illustration and not of limitation.

Example 1

Rigid PLA Film

A PLA hydrosol is made by blending and homogenizing 22 g of Ecorene™ NW31-100 powder available through ICO Polymers, 0.5 g of Triton™ X-100 (Octyl phenol ethoxylate) available through Dow Chemical Company, and 40 g of water in an IKA Ultra Turrax T-25 rotor/stator assembly. A thin layer of the PLA hydrosol is deposited on a lab scale cast aluminum plate. The PLA formed a clear strong coherent rigid film, after drying and fusion of the dispersion after deposition on the aluminum plate.

Example 2

Flexible Octyl Phenol Ethoxylate Plasticized Film

A PLA hydrosol is prepared by blending and homogenizing 27.4 g of Ecorene NW61-100 PLA powder, 16.5 g of Triton X-100 (Octyl phenol ethoxylate) and 59 g of water in an IKA Ultra Turrax T-25. A thin layer of the PLA hydrosol is deposited on a lab scale cast aluminum plate. The PLA hydrosol on the plate was dried in an oven at about 85° C., then fused at 125° C. The PLA formed a clear, strong, and flexible film.

A PLA hydrosol is prepared by blending and homogenizing 28 g of Ecorene NW61-100 PLA powder, 16 g of Triton X-100 (Octyl phenolethoxylate) and 56 g of water in an IKA Ultra Turrax T-25. The dispersion is degassed in vacuum. A ceramic plate was pre-heated to 85° C.-90° C., then gently dipped into the PLA hydrosol and repeated one more time after partial drying to obtain a thick film. The film is then dried at about 85° C. and fused at 125° C. in an oven for 20 minutes. The film formed is clear, strong and flexible as the cast film above.

Example 3

Variation of Flexible Octyl Phenol Ethoxylate Plasticized Film

A PLA hydrosol is prepared by blending and homogenizing 20 g of Ecorene NW61-100 PLA powder, 5 g of Triton X-100 (Octyl phenolethoxylate) and 35 g of water in an IKA Ultra Turrax T-25. The film required higher fusion temperature than the cast film in Example 2 to form a coherent film.

Example 4

Variation of Flexible Octyl Phenol Ethoxylate Plasticized Film

A PLA hydrosol is prepared by blending and homogenizing 30 g of Ecorene NW61-100 PLA powder, 20 g of Triton X-100 (Octyl phenolethoxylate) and 70 g of water in an IKA Ultra Turrax T-25. The film is dried and fused as the cast film in Example 2. The film formed is clear and more flexible than in Example 3.

Example 5

Flexible Polyethylene Glycols Plasticized PLA Film

A PLA hydrosol is prepared by blending and homogenizing 20 g of Ecorene NW61-100 PLA powder, 5.3 g of PEG 400 (polyethylene glycol), 0.5 g of Triton X-100 and 35 g of water in an IKA Ultra Turrax T-25. A thin layer of the PLA hydrosol is deposited on a lab scale cast aluminum plate. The PLA hydrosol on the plate was dried at about 85° C. and fused at 125° C. in an oven for about 20 minutes. The film was clear and flexible but showed a slight oily surface texture.

Examples 6

Variation of Flexible Polyethylene Glycols Plasticized PLA Film

A PLA hydrosol is prepared by blending and homogenizing 20 g of Ecorene NW61-100 PLA powder, 5 g of PEG 3350, 0.5 g of Triton X-100 and 38 g of water in an IKA Ultra Turrax T-25. The film prepared after degassing, drying and fusion indicated a flexible, slightly waxy texture.

Examples 7

Variation of Flexible Polyethylene Glycols Plasticized PLA Film

A PLA hydrosol is prepared by blending and homogenizing 20 g of Ecorene NW61-100 PLA powder, 5 g of PEG 800, 0.5 g of Triton X-100 and 38 g of water in an IKA Ultra Turrax T-25. The film is coherent, clear and flexible.

Examples 8

Variation of Flexible Polyethylene Glycols Plasticized PLA Film

A PLA hydrosol is prepared by blending and homogenizing 20 g of Ecorene NW61-100 PLA powder, 5 g of PEG 20000, 0.5 g of Triton X-100 and 38 g of water in an IKA Ultra Turrax T-25. The film is coherent, clear and flexible.

Examples 9

Flexible Citrate Ester Plasticized PLA Film

A PLA hydrosol is prepared with 20 g of Ecorene NW31-100 PLA powder, 5 g of Citroflex A4 (available through Vertellus Specialties Inc.), 0.7 g of Triton X-100 and 35 g of water. The film prepared after drying and fusion formed is clear and flexible. The film has a slight oily texture.

Examples 10

Variation of Flexible Citrate Ester Plasticized PLA Film

A PLA hydrosol is prepared with 20 g of Ecorene NW31-100 PLA powder, 10 g of Citroflex A4 (available through Vertellus Specialties Inc.), 0.7 g of Triton X-100 and 35 g of water. A flexible film is formed after drying and fusion.

Examples 11

Variation of Flexible Citrate Ester Plasticized PLA Film

A PLA hydrosol is prepared with 20 g of Ecorene NW31-100 PLA powder, 20 g of Citroflex A4 (available through Vertellus Specialties Inc.), 0.7 g of Triton X-100 and 35 g of water. The film prepared is very flexible but the plasticizer seem to migrate out of the film on standing.

Example 12

Flexible PLA Film with Multiple Plasticizers

A PLA hydrosol is prepared with 12 g of Ecorene NW31-100 PLA powder, 4.8 g of Ecorene NW61-100 PLA powder, 9.6 g of Citroflex A4, 8.4 g of PEG 400, 2 g of Triton X-100 and 45 g of water. The PLA hydrosol displayed a high viscosity. A film cast from it is flexible and clear after drying and fusion.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A glove comprising:
   at least one layer of an elastomeric material, wherein the elastomeric material comprises:
   a blend of
      a polylactic acid (PLA) polymer; and
      a non-ionic surfactant comprising an octyl phenol ethoxylate; and
      a biodegradable polymer resin selected from the group consisting of homopolymer, block copolymer, graft copolymer and random copolymer,
   wherein each homopolymer, block copolymer, graft copolymer and random copolymer comprises one of polyglycolic acid, polycaprolactone, polyhydroxybutyrate, a non-polylactic acid aliphatic polyester, polyalkylene ester, polyester amide, polyvinyl ester, polyester carbonate, polyvinyl alcohol, polyanhydride and polysaccharide.

2. A glove according to claim 1 wherein the elastomeric material further comprises a plasticizer that does not comprise an octyl phenol ethoxylate.

3. A glove according to claim 2, wherein the plasticizer is selected from the group consisting of a polyethylene glycol, a polypropylene glycol, a fatty acid ester, a citric acid ester, a lactide monomer, an epoxidised oil, an adipate ester, an azealate ester, an acetylated coconut oil and any combinations thereof.

4. A glove according to claim 1, wherein the octyl phenol ethoxylate provides a dual function of the non-ionic surfactant and a plasticizer.

5. A glove according to claim 4, wherein the elastomeric material further includes a polyethylene glycol, wherein the polyethylene glycol also provides the dual function of a non-ionic surfactant and a plasticizer.

6. A glove according to claim 1 wherein the elastomeric material further comprises at least one of a defoaming agent, a cross-linking agent, a chain extender, an aging and hydrolytic stabilizer for PLA, a flavoring component, an antimicrobial agent, a detackifying agent, a botanical extract, a donning enhancing agent, a colorant component, and a therapeutic component.

7. A glove according to claim 6 wherein the flavoring component is xylitol.

* * * * *